United States Patent [19]
Cochran et al.

[11] Patent Number: 6,080,889
[45] Date of Patent: Jun. 27, 2000

[54] PRODUCTION OF TERTIARY AMINE OXIDES

[75] Inventors: Rebecca S. Cochran, Baton Rouge, La.; Andrea P. Wight, Pasadena, Calif.; Douglas H. Krzystowczyk, Orangeburg, S.C.; Dustin H. Thomas, Baton Rouge, La.

[73] Assignee: Albemarle Corporation, Richmond, Va.

[21] Appl. No.: 09/053,444

[22] Filed: Apr. 1, 1998

[51] Int. Cl.⁷ .................................................. C07C 291/00
[52] U.S. Cl. ........................................................... 564/298
[58] Field of Search ............................................... 564/298

[56] References Cited

U.S. PATENT DOCUMENTS

| | | | |
|---|---|---|---|
| 3,332,999 | 7/1967 | Mitchell et al. | 260/583 |
| 4,247,480 | 1/1981 | Murata et al. | 564/298 |
| 4,748,275 | 5/1988 | Smith et al. | 564/298 |
| 4,960,934 | 10/1990 | Smith et al. | 564/298 |
| 4,970,340 | 11/1990 | Smith | 564/298 |
| 5,075,501 | 12/1991 | Borland et al. | 564/297 |
| 5,082,940 | 1/1992 | Legrand et al. | 544/353 |
| 5,130,488 | 7/1992 | Smith et al. | 564/298 |
| 5,208,374 | 5/1993 | Borland et al. | 564/298 |
| 5,223,644 | 6/1993 | Blezard et al. | 564/2 |
| 5,292,954 | 3/1994 | Borland et al. | 564/298 |
| 5,442,113 | 8/1995 | Blezard et al. | 564/2 |
| 5,466,870 | 11/1995 | Miller et al. | 564/298 |
| 5,498,373 | 3/1996 | Miller et al. | 252/546 |
| 5,498,791 | 3/1996 | Blezard et al. | 564/2 |
| 5,710,333 | 1/1998 | Bader et al. | 564/298 |

FOREIGN PATENT DOCUMENTS

| | | |
|---|---|---|
| 307184 | 3/1989 | European Pat. Off. . |
| 032069 | 6/1989 | European Pat. Off. . |

OTHER PUBLICATIONS

WPIDS Abstract of JP 51032505, dated Mar. 19, 1976.
CAPLUS Abstract of JP 51032505, dated Mar. 19, 1976.

*Primary Examiner*—Peter O'Sullivan
*Attorney, Agent, or Firm*—E. E. Spielman, Jr.

[57] ABSTRACT

Exothermic oxidation of tertiary amine with aqueous hydrogen peroxide in an aqueous reaction medium formed or being formed from tertiary amine, aqueous hydrogen peroxide, carbon dioxide, and optionally chelating agent and/or additional water, is initiated at about 15 to about 25° C., and while agitating the reaction mixture, the temperature is allowed to rise adiabatically to a temperature in the range of about 50 to about 100° C. In this way, it is possible to produce tertiary amine oxides with very low levels, if any, of nitrosamine impurity, without addition of metal and/or phosphorus-containing components recommended in the prior art. Even though a substantial portion of the reaction is performed at temperatures in the range of about 50–100° C., nitrosamine content, if any, in the resultant tertiary amine oxide product can be well below 30 ppb. Use of such relatively exothermically achieved high temperatures in turn results in faster reaction rates and enables use of shorter reaction periods.

37 Claims, No Drawings

PRODUCTION OF TERTIARY AMINE OXIDES

TECHNICAL FIELD

This invention relates to novel process technology for producing tertiary amine oxides and to novel and eminently useful tertiary amine oxide compositions which are provided by this invention. When properly carried out, the process technology of this invention enables the direct synthesis and provision of tertiary amine oxide surfactants having extremely low levels, if any, of nitrosoamines (commonly known as nitrosamines), as well as possessing other important characteristics.

BACKGROUND

Typically, amine oxides are produced by combining a tertiary amine and hydrogen peroxide in the presence of water. The typical prior art process, whether or not a reaction promoter is employed, is an isothermal process wherein the amine and water, and promoter if used, are heated before addition of peroxide in order to initiate the reaction. Because the reaction is exothermic, once the reaction has been initiated by heat input, the reaction mixture must be cooled to control the temperature of the reaction. After the majority of the reaction is completed, additional heat must be added to the system to achieve a final conversion.

When the typical prior art amine oxide process is carried out at temperatures above 60° C., significant amounts of nitrosamines are produced. Nitrosamine impurities in amine oxides have long been regarded as harmful impurities by most in the surfactant industry because of suspected carcinogenic and mutagenic properties. See for example "Nitrosamines: Assessing the Relative Risk" in *Chemical & Engineering News*, pages 20–26, Mar. 31, 1980. Nevertheless, according to U.S. Pat. No. 5,498,791 (Mar. 12, 1996), commercial amine oxides contain between 200–1000 ppb nitrosamines.

Heretofore various attempts have been made to reduce the levels of nitrosamines in amine oxides. According to U.S. Pat. No. 5,223,644 (Jun. 29, 1993): "The method generally recommended in the prior art for reducing the nitrosamine levels has been to carry out the reaction at relatively low temperatures, e.g. below 40° C., using the carbon dioxide catalyst to maintain adequate reaction rates. We have found in practice, however, that this approach is not generally effective to produce amine xides with the desired low nitrosamnine content, especially when excess of hydrogen peroxide is used, as has been normal practice to avoid products contaminated with substantial residual unreacted amnine." It appears that the prior art referred to in the foregoing quotation is EP 307 184 A2, published Mar. 15, 1989, wherein it is pointed out that tert-amine oxides that are substantially free of nitrosamine impurities can be made by reacting the desired tert-amines with aqueous hydrogen peroxide in the presence of a promoter formed from carbon dioxide if the reaction is conducted at a temperature of 45° C., or lower and preferably below 40° C.

In U.S. Pat. No. 5,223,644, it is proposed to inhibit nitrosamine formation in tertiary amines to levels below 100 ppb and preferably below 50 ppb by including in the tert-amine/hydrogen peroxide reaction mixture or in the resultant tert-amine oxide greater than about 2.5% and up to 20% by weight of the tert-amine of a bicarbonate or carbonate such as an alkali or alkaline earth metal bicarbonate or carbonate, notably sodium bicarbonate.

U.S. Pat. Nos. 5,442,113 (Aug. 15, 1995) and 5,498,791 (Mar. 12, 1996), acknowledge that the use of such relatively high concentrations of carbonates and/or bicarbonates (greater than 2.5% by weight of the amine) to inhibit the formation of nitrosamines "may result in levels of inorganic impurity in the product which are unacceptable to some customers." The approach taken in these two patents is to employ a synergistic mixture of alkali or alkaline earth metal bicarbonate or carbonate such as sodium bicarbonate, with a phosphonate such as an organoamino methylene phosphonate.

It would be of great advantage if a way could be found of inhibiting formation of nitrosamines during production of tert-amine oxides by the oxidation of tert-amine with hydrogen peroxide without need for addition of metal or phosphorus compounds and consequent contamination of the product with such impurities, especially if the reaction could be safely carried out using temperatures above 40–45° C. This invention is deemed to fulfill these needs in a highly effective manner.

THE INVENTION

It has been discovered, inter alia, that it is possible to produce tertiary amine oxides with very low levels, if any, of nitrosamine impurity, by oxidation of tertiary amine with aqueous hydrogen peroxide without addition of metal and/or phosphorus-containing components. Moreover, it has been found possible to conduct a substantial portion of the reaction at temperatures in the range of about 50 to about 100° C., while at the same time maintaining very low levels of nitrosamine content, if any, in the resultant tertiary amine product. Use of such relatively high temperatures in turn results in faster reaction rates and enables use of shorter reaction periods. And, as a consequence of this invention, it is now possible to provide highly pure tertiary amine oxide products which have very low levels, if any, of nitrosamine impurities, and very low levels of metal impurities, and because no phosphorus additives are needed in the process, the tertiary amine oxide products of this invention are devoid of phosphorus resulting from use of phosphorus additive. Since it is preferred not to employ organic solvents or diluents in the aqueous reaction medium, this invention also makes it possible to provide tertiary amine oxide products that are devoid of organic impurities resulting from use of organic solvent or diluent in the process. Moreover, all of these advantages can be achieved in operations readily, efficiently, and safely conducted on an industrial plant scale.

Thus, in accordance with one of the embodiments of this invention there is provided a process for producing tertiary amine oxide which comprises oxidizing tertiary amine with hydrogen peroxide in an aqueous reaction medium, the aqueous reaction medium having been formed or being formed from tertiary amine, aqueous hydrogen peroxide, carbon dioxide, and optionally chelating agent and/or additional water, the exothermic oxidation reaction being initiated at a temperature in the range of about 15 to about 25° C., and while agitating the reaction mixture, allowing the temperature of the reaction mixture to rise adiabatically to a temperature in the range of about 50 to about 100° C., such that tertiary amine oxide is produced. Preferably the reaction is conducted in a thermally insulated reactor. Products having 30 ppb or less, if any, of nitrosamine impurity can be produced by proper conduct of the process of this invention.

Without being bound by theory, it is believed that a tenable explanation for the surprisingly low levels, if any, of nitrosamine impurity in the product results from substantially uniform temperatures and substantially uniform rate of temperature increase being developed throughout the entire reaction mixture as a result of the exothermic reaction taking place throughout the entire suitably-agitated reaction mixture. In other words, significant differences in temperature within the reaction mixture at each given increment of time, such as localized higher temperature regions in the reaction mixture close to the reactor walls as compared to the temperature of interior portions of the reaction mixture at any given instant of time, are minimized by suitable agitation and avoidance of external heat input through the reactor walls. Likewise, heat input to the reaction mixture via internal heating coils resulting in cooler regions of reaction mixture close to reactor walls and rapid flow of heat through the reactor walls are avoided. Thus, once the reaction has been initiated, the temperature of the reaction mixture continuously rises due to the exothermic nature of the reaction, yet at each given instant of time the temperature is deemed substantially uniform throughout the entire reaction mixture.

It will be seen, therefore, that the above embodiment of this invention takes full advantage of the exotherm produced by the oxidation of tertiary amine to tertiary amine oxide by hydrogen peroxide. In this way, the need to supply heat energy to the reaction is eliminated and the amount of energy consumed in the process is minimized. In contrast, U.S. Pat. Nos. 5,442,113 and 5,498,791 (supra) regard the exotherm as a problem to be avoided.

Again, without being bound by theory, in addition to the above-referred-to temperature uniformity in the reaction mixture, other factors are believed to also contribute to the excellent results achievable by use of the process technology of this invention. Uniform reaction temperatures within the system above 40° C., utilizing carbon dioxide as catalyst and utilizing excess hydrogen peroxide produce amine oxide with low residual free amine and with low nitrosamine levels. Because the catalyst, carbon dioxide, acts as a neutralizing agent to the amine, the basicity of the solution is reduced, thus stabilizing the peroxide in the reaction solution. The stabilizing effects of the carbon dioxide in turn allow the reaction to be carried out at higher temperatures without excessive peroxide decomposition. Moreover, because the catalyst acts as a neutralizing agent, the amine, water, and peroxide solution are able to form an emulsion which leads to faster and more uniform reaction initiation and progression.

Although less preferable, another embodiment of this invention simulates to the extent reasonably feasible technically and economically, the conditions that exist during the adiabatic process of this invention. In this additional embodiment there is provided a process for producing tertiary amine oxide which comprises oxidizing tertiary amine with hydrogen peroxide in an aqueous reaction medium, the aqueous reaction medium having been formed or being formed from tertiary amine, aqueous hydrogen peroxide, carbon dioxide, and optionally chelating agent and/or additional water, the exothermic oxidation reaction being initiated at a temperature in the range of about 1 to about 25° C., and while agitating the reaction mixture, applying a controlled limited amount of heat energy to the reaction mixture and maintaining a substantially uniform temperature throughout the agitated reaction mixture whereby at any given moment in time the temperature differential within the reaction mixture is no greater than 5° C., and preferably no greater than 2° C., such that the temperature of the reaction mixture is increased, and preferably is progressively increased, to a maximum temperature in the range of about 50 to about 100° C., such that tertiary amine oxide is produced, the major amount (i.e., more than 50%) of the heat energy causing the increase in temperature of the reaction mixture being derived from the exothermic reaction itself, with the balance of the thermal energy causing such temperature increase (i.e., less than 50%) being supplied by the application of said controlled limited amount of thermal energy to the reaction mixture. By proper selection and coordination of the reaction initiation temperature, the volume of water in the reaction mixture, the amount of heat energy supplied to the reaction mixture, and the rate of agitation of the reaction mixture, it is possible to produce tertiary amine oxides having very low levels of nitrosamine content without need for use of special additives such as metal carbonates or bicarbonates, and/or phosphorus additives of the prior art.

Still another embodiment of this invention provides an aqueous solution of tertiary amine oxide wherein the content of tertiary amine oxide is in the range of about 25 to about 35 wt %; wherein the content of nitrosamine, if any, is 30 ppb (wt/wt) or less; wherein the content of amine, if any, is 0.3 wt % or less; wherein the total content of alkali metal (e.g., Na), if any, is 10 ppm (wt/wt) or less; and wherein the total content of alkaline earth metal, if any, (e.g., Mg and Ca) is 1 ppm (wt/wt) or less; each foregoing wt %, ppb, and ppm being based on the weight of the solution. So far as is known, it has never been possible heretofore to prepare a tertiary amine oxide solution having these attributes and characteristics by use of any previously described process, muchless one involving the oxidation of a tertiary amine by aqueous hydrogen peroxide. In this connection, as used anywhere in the specification or claims hereof "ppb" means parts per billion parts, a billion being $10^9$ or a thousand million; "ppm" means parts per million parts, a million being $10^6$; and as indicated by "wt/wt" the parts are parts by weight. In addition to the foregoing attributes and characteristics, the solutions of this invention preferably have a content, if any, of no more than about 1 wt % hydrogen peroxide, and more preferably no more than about 0.5 wt % hydrogen peroxide, based on the weight of the solution. Also preferred are solutions wherein the content of titanium, if any, is 0.1 ppm (wt/wt) or less; wherein the content of iron, if any, is 1.0 ppm (wt/wt) or less; wherein the content of cobalt, if any, is 0.3 ppm (wt/wt) or less; wherein the content of nickel, if any, is 0.5 ppm (wt/wt) or less; and wherein the content of copper, if any, is 2 ppm (wt/wt) or less, and most preferably 0.5 ppm or less.

Preferred solutions are those in which the tertiary amine oxide is one or more compounds of the formula $$R^1R^2R^3N=O$$

where $R^1$ is a methyl or ethyl group, $R^2$ is a primary alkyl group having in the range of about 8 to about 20 carbon atoms, and $R^3$ is, independently, a methyl group, an ethyl group, or a primary alkyl group having in the range of about 8 to about 20 carbon atoms. Compounds of this formula wherein $R^1$ and $R^3$ are methyl groups and $R^2$ is a straight chain primary alkyl group are particularly preferred. Among the distinct advantages of these solutions is that they pose no known potential health hazard in use, they are extremely friendly to the environment, they leave essentially no residues during use, and they can be used in formulating a wide variety of surfactant compositions that possess good lime dispersant properties and very low destabilizing properties toward bleaches such as sodium hypochlorite.

The above and other embodiments and features of this invention will be still further apparent from the ensuing description and appended claims.

Tertiary Amine

The amines that may be used in the process of our invention are typically linear amines of the general formula $R^1R^2R^3N$, wherein $R^1, R^2$, and $R^3$ represent straight or branched chain alkyl groups, alkenyl groups or aralkyl groups which may be the same or different. They may be lower alkyl groups, i.e., of from 1 to 7, preferably 1 to 4, carbon atoms, but in a preferred embodiment of this invention, the tertiary amines may instead be represented by the general formula $(R)_m R^1)_n N$, wherein m=1 or 2 and n=(3-m). In this latter formula, the groups designated R, which may be the same or different, represent $C_8-C_{24}$ alkyl or alkenyl polyalkyleneoxy groups, $C_7-C_{23}$ esteralkyl or esteralkenyl groups, amidoalkyl or amidoalkenyl groups, and the $R^1$ groups, which may also be the same or different, represent $C_1-C_4$ alkyl, alkoxy orhydroxyalkyl, or polyalkyleneoxy groups. The polyalkyleneoxy groups are preferably polyethyleneoxy groups or polypropyleneoxy or mixed ethyleneoxy and propyleneoxy groups containing between 1 and 20 ethyleneoxy and/or propyleneoxy groups. The amidoalkyl groups are preferably $C_7-C_{23}$ alkylamidopropyl groups or alkenylamidopropyl groups.

Alternatively, the amines may comprise cyclic amines such as imidazolines or pyridines, N-substituted piperazines, or N-substituted morpholines, e.g., N-methyl morpholine.

Preferred tertiary amines used in the process of this invention are one or more compounds of the formula $R^1R^2R^3N$ where $R^1$ is a methyl or ethyl group, $R^2$ is a primary alkyl group having in the range of about 8 to about 20 carbon atoms, and $R^3$ is, independently, a methyl group, an ethyl group, or a primary alkyl group having in the range of about 8 to about 20 carbon atoms. Compounds of this formula wherein $R^1$ and $R^3$ are methyl groups and $R^2$ is a straight chain primary alkyl group are particularly preferred. Dimethyl decyl amine, dimethyl dodecyl amine and dimethyl tetradecyl amine are especially preferred reactants for use in preparing aqueous surfactant solutions pursuant to this invention.

Hydrogen Peroxide

As noted above, the hydrogen peroxide is typically employed as a water solution of any suitable concentration. Preferably the hydrogen peroxide is employed as a 30 to 70 wt % aqueous solution. Particularly preferred solutions are 30 to 40 wt % aqueous hydrogen peroxide solutions. The amount of hydrogen peroxide employed in the reaction should be at least a stoichiometric amount (i.e., at least 1 mole of hydrogen peroxide per mole of tertiary amine). Preferably an excess amount of hydrogen peroxide is used, and in this case an excess in the range of about 1.01 to about 1.2 moles of hydrogen peroxide per mole of tertiary amine is preferred. It is especially preferred to employ these reactants in a mole ratio of about 1.01 to about 1.05 mole of hydrogen peroxide per mole of tertiary amine. These latter ranges when utilized in the practice of this invention make it possible to form a finished product having an extremely low content of both free amine and hydrogen peroxide impurities.

Chelating Agent

An optional, but preferable, component used in the reaction mixtures is at least one suitable chelating agent such as ethylenediamine tetraacetic acid or a water-soluble salt thereof, diethylenetriamine pentaacetic acid or a water-soluble salt thereof, or S,S-ethylenediamine disuccinic acid or a water-soluble salt thereof. Other suitable chelating agents include nitrilotriacetic acid or a water-soluble salt thereof. The chelating agent, which serves as a sequestrant for metal ions which may be derived by extraction from metallic reactor walls, piping or the like, is preferably a metal-free chelating agent. In this way the chelating agent as added to the reaction mixture does not itself introduce any metal constituent(s). Thus, if used as a salt, it is preferably an ammonium salt, although because of the small amounts of chelating agent used, alkali metal salts such as the sodium salts are acceptable for use. Typically, the amount of chelating agent used will fall in the range of about 0.01 to about 0.1 wt %, and preferably in the range of about 0.05 to about 0.1 wt %, based on the total weight of the reaction mixture.

Of the chelating agents suitable for use, ethylenediamine tetraacetic acid, diethylenetriamine pentaacetic acid, and S,S-ethylenediamine disuccinic acid are the three most preferred materials.

Water

For best results the water used should be free of appreciable quantities of dissolved metals. While it is not necessary to employ deionized or distilled water, such materials can be used if desired. Ordinary tap water is satisfactory provided that it has a metallic content, if any, of not more than 5 ppm. Ordinarily at least a portion of the water employed in producing the reaction medium will be provided by the aqueous hydrogen peroxide solution. However, oftentimes it is desirable to increase the amount of water over and above that provided by the aqueous hydrogen peroxide being used in making up the reaction mixture. In general, the amount of water should correspond in quantity to the quantity desired in the finished amine oxide solution to be produced in the process, as this eliminates the need for subsequent operations such as further dilution with water, or distillation of excessive quantities of water from the aqueous product solution produced in the reaction. Thus, if a 30 wt % solution of amine oxide is the target product, the total amount of water introduced into the reaction mixture should correspond to approximately 70 wt % of the projected total weight of the amine oxide solution being formed.

Carbon Dioxide

An essential ingredient charged to the reaction mixture is carbon dioxide. Although it may be charged in the form of so-called dry ice, it is preferable to introduce the carbon dioxide in gaseous form and to introduce the same at a locus below the surface of the liquid reaction mixture. The carbon dioxide serves as a reaction catalyst or reaction promoter. In this connection, the precise chemical make-up of the carbon dioxide-derived catalyst is not known with certainty. It may be that the carbon dioxide itself catalyzes or promotes the reaction. However, it is equally possible that the carbon dioxide reacts in situ to form either carbonic acid or some unidentified complex or other substance which serves as the actual catalytic entity. It will thus be understood that this invention is not limited to the particular form or chemical composition of the reaction catalyst or reaction promoter resulting from the introduction into the reaction mixture of carbon dioxide as an ingredient.

Typically, the amount of carbon dioxide introduced into the aqueous reaction mixture should be such as to result in the reaction mixture initially achieving a pH in the range of about 7 to about 8, and preferably in the range of about 7.3 to about 7.8.

Modes of Addition

The various ingredients making up the reaction mixture can be introduced into the reactor in a number of sequences. For example each of the ingredients (tertiary amine, aqueous hydrogen peroxide, carbon dioxide, additional water if used, and chelating agent if used) can be introduced individually or in any suitable subcombinations and in any suitable order into the reactor in the total quantities to be used with no further feed of any ingredient during the course of the reaction. When conducting the reaction in this manner (i.e., with all of the ingredients charged at the outset), the only preference is that either the carbon dioxide or the aqueous hydrogen peroxide should be the last ingredient introduced into the reaction mixture, as the reaction will be initiated upon the introduction of either such ingredient to the mixture comprising the other such ingredient and the tertiary amine. Thus, in one such embodiment the aqueous reaction medium is formed by mixing together tertiary amine, carbon dioxide, optionally chelating agent, and optionally water, and then introducing aqueous hydrogen peroxide into the reaction mixture to initiate the exothermic reaction. In another such embodiment the aqueous reaction medium is formed by mixing together tertiary amine, aqueous hydrogen peroxide, and optionally chelating agent and/or additional water, and then introducing carbon dioxide to initiate the exothermic reaction. Still another such embodiment involves forming the reaction mixture by introducing tertiary amine, and optionally chelating agent and/or water, into a reactor, and then introducing concurrently or in any sequence, aqueous hydrogen peroxide and carbon dioxide to initiate the exothermic reaction. In theory, the tertiary amine could be the last ingredient charged to the reaction mixture, however this is less desirable as it could result in excessive premature oxidation of the tertiary amine with adverse consequences.

Instead of charging all of the reactants at the outset it is possible, and in some cases preferable, to introduce one or more of the ingredients to the reaction mixture portionwise, and continuously and/or intermittently, as the reaction proceeds. In this mode of addition there are various preferred embodiments. In one such embodiment the aqueous hydrogen peroxide is introduced portionwise, continuously and/or intermittently, into the reaction mixture initially composed of tertiary amine, carbon dioxide, chelating agent if used, and water if used. Some of the hydrogen peroxide can also be present in the initial reaction mixture. In another such embodiment aqueous hydrogen peroxide and carbon dioxide are concurrently introduced portionwise, continuously and/or intermittently, into the reaction mixture initially composed of tertiary amine, chelating agent if used, and water if used. Here again aportion of the carbon dioxide and/or hydrogen peroxide can be present in the initial reaction mixture. Still another variant is to introduce carbon dioxide portionwise, continuously and/or intermittently, into the reaction mixture initially composed of tertiary amine, aqueous hydrogen peroxide, chelating agent if used, and additional water if used. Once again the initial reaction mixture may also contain a portion of the carbon dioxide.

Accordingly, this invention contemplates the addition of the respective ingredients into the reaction mixture being formed in any suitable manner (individually and/or in any suitable subcombination(s), concurrently and/or in any suitable sequence.

Thermal Insulation

Preferably the reactor used in the practice of the process of this invention is provided with thermal insulation of any suitable type. The use of thermal insulation having a suitably high R value reduces the extent to which thermal energy can pass into or out of the reaction vessel and thus into or out of the reaction mixture undergoing an adiabatic reaction. In the embodiment of this invention wherein an adiabatic reaction is simulated, a jacketed reactor can be employed in which a controlled amount of heat energy is supplied to the reaction mixture by means of the heated fluid flowing through the jacket of the reactor. Preferably, as the temperature of the reaction mixture rises by virtue of the exothermic reaction, the temperature of the water fed to and flowing through the jacket is correspondingly elevated so that the amount of heat loss or gain through the reactor walls is minimized.

While it is preferred to employ a thermally insulated reactor when conducting the process of this invention, this is not required. The process of this invention can be carried out effectively in conventional reactors devoid of any special thermal insulation, especially when the reaction mixture is suitably agitated to ensure substantially uniform composition throughout the reaction mixture undergoing adiabatic reaction.

Agitation

In order to ensure that at any given moment of time the temperature within the entire reaction mixture is substantially the same, it is important to suitably agitate the reaction mixture to form a substantially uniform emulsion or emulsion-like reaction mixture. In this way, the reaction tends to take place substantially uniformly at all locations within the reaction mixture, which in turn results in a progressive increase in the substantially uniform temperature of the reaction mixture. Thus, it is desirable to employ a reactor equipped with suitable mechanical stirring apparatus. However, other forms of agitation such as use of a rocking autoclave are also feasible.

Temperature and Pressure Conditions

In the embodiments wherein the process of this invention is conducted completely adiabatically, the exothermic oxidation reaction is initiated at a temperature in the range of about 15 to about 25° C., and while agitating the reaction mixture, allowing the temperature of the reaction mixture to rise adiabatically to a temperature in the range of about 50 to about 100° C., and preferably in the range of about 60 to about 80° C., such that tertiary amine oxide is produced. In the embodiments where a major amount (i.e., more than 50%) of the heat energy causing the increase in temperature of the reaction mixture is derived from the exothermic reaction, with the balance of the thermal energy causing such temperature increase (i.e., less than 50%) being supplied by the application of a controlled limited amount of thermal energy, the reaction is initiated at a temperature in the range of about 1 to about 25° C., and while agitating the reaction mixture and keeping the temperature substantially uniform throughout the entire mixture at each moment in time, a controlled limited amount of heat energy is applied to the reaction mixture to a maximum temperature in the range of about 50 to about 100° C., such that tertiary amine oxide is produced. In all such embodiments the reaction can be conducted in an open system at ambient atmospheric pressure, or it can be conducted in a closed system under superatmospheric pressure such as autogenous pressure or externally applied pressure.

Analytical Procedures

Any suitable procedure can be used for determining content various impurities in the reaction mixtures produced in the process. For convenience, the following procedures (or other procedures of at least equivalent accuracy) are recommended:

To determine free amine in the aqueous solution of tertiary amine oxide, a sample of amine oxide is reacted with acetic anhydride in the presence of acetic acid under reflux conditions. The sample is cooled and titrated potentiometrically with 0.1N $HClO_4$ in acetic acid.

To determine alkali metal or alkaline earth metal content in the aqueous solution of the tertiary amine oxide, a sample of aqueous amine oxide is digested with sulfuric acid at 380° C. Nitric acid is added as needed to keep the solution clear.

The mixture is charred until only 1 mL remains in the beaker. Deionized-distilled water and concentrated nitric acid are added to form a solution. The mixture is allowed to again cool. The resulting solution is analyzed by inductively coupled plasma (ICP) emission spectroscope using a Plerkin-Elmer Optima 3000, or equivalent device.

To determine titanium, iron, cobalt, nickel, and copper content in the aqueous solution of the tertiary amine oxide, a sample of aqueous amine oxide is digested with sulfuric acid at 380° C. Nitric acid is added as needed to keep the solution clear. The mixture is charred until only 1 mL remains in the beaker. Deionized-distilled water and concentrated nitric acid are added to form a solution, and the mixture is allowed to again cool. The resulting solution is analyzed by inductively coupled plasma (ICP) emission spectroscopy. For this analysis, a Perkin-Elmer Optima 3000, or equivalent device is employed.

To determine hydrogen peroxide in the aqueous solution of the tertiary amine oxide, a dilute sample of aqueous amine oxide is reacted with potassium iodide and titrated with sodium thiosulfate. A quantitative amount of iodine is formed from the available peroxide in a given sample.

Total N-nitrosamine content (TNC) is determined by a chemiluminescence method in which nitrite ions in the sample are destroyed by sulfuric acid, the sample is denitrosated using HBr/acetic acid, and the nitric oxide (NO) liberated from the sample is fed into a chemiluminescence analyzer. The nitric oxide reacts with ozone in the analyzer to produce excited $NO_2$. As the $NO_2$ decays to the ground state, light is emitted in the near infrared region, and this signal can be integrated electronically. It has been reported that the limit of detection by this method is 10 ppb reported as the —NNO species (mw=44).

The following examples are illustrative of ways by which the process of this invention can be carried out. These examples are not intended to limit, and should not be construed as limiting, the invention to the particular procedures described.

EXAMPLE 1

The following general procedure for the conduct of an adiabatic process typically produces amine oxides containing <30 ppb total nitrosamines. Dimethyl decyl amine (ADMA®-10 amine; Albemarle Corporation) (200.3 g, 1.08 mol), 35% aqueous hydrogen peroxide (108.1 g, 1.11 mol, 4% molar excess), 409.8 mL of water, and diethylene triamine pentaacetic acid (DTPA) (0.5 g, 1.3 mmol), are added to an thermally insulated round bottom flask. The insulation is a mantle of fiberglass wool. Carbon dioxide is introduced to the reactor in 1.6 wt % relative the charged amine. Introduction of a sufficient amount of $CO_2$ catalyst is indicated by reduction in the pH of the amine/water mixture to a pH of 7.5–7.8. Continuous supply of catalyst is not necessary if enough is introduced initially. The reaction quickly initiates and is allowed to continue adiabatically to the maximum temperature caused by the exotherm. The maximum temperature in reactions carried out in this manner and scale is typically 75–80° C., and is typically achieved in about 20 to 30 minutes after introduction of the $CO_2$ catalyst. The temperature remains high and no cooling is applied until the reaction mass contains <0.3 wt % residual free amine. The reaction is typically completed within 2 hours of catalyst introduction. Over the two-hour period, the temperature decreases to about 62° C. In a reaction carried out in this manner, the total nitrosamine content in the aqueous product solution of dimethyl decyl amine oxide, as measured by chenliluminescence, was 11 ppb (wt/wt).

EXAMPLE 2

A procedure similar to that of Example 1, but in which the hydrogen peroxide is metered into the reaction mixture over time produces like results. Thus, dimethyl decyl amine (ADMA®-10 amine; Albemarle Corporation) (201.8 g, 1.09 mol), 410.0 mL of water, and diethylene triamine pentaacetic acid (DTPA) (0.5 g, 1.3 mmol), are added to a thermally insulated round bottom flask. The flask is insulated with glass wool. The organic/water mixture is treated with carbon dioxide prior to charging the hydrogen peroxide. The 35% aqueous hydrogen peroxide (108.6 g, 1.12 mol, 4% molar excess) is charged over a period of 35 minutes along with additional carbon dioxide. During that period the temperature rises 54° C. The maximum temperature achieved was 74° C. During the 90-minute cook, the temperature decreased by 11° C. Two hours after the peroxide addition began, the free amine was measured to be 0.21 wt % (99.2% conversion) and the residual hydrogen peroxide was 0.25 wt %. The level of nitrosamine was 10 ppb (wt/wt).

EXAMPLE 3

Combined in a round bottom flask at ambient temperature (ca. 20° C.) were 191.2 grams (0.90 mol) of dimethyl dodecyl amine (ADMA®-12 amine, Albemarle Corporation), 393.3 grams of tap water (essentially zero hardness), and 0.5 gram of DTPA. The flask was insulated with a mantle of glass wool. Catalyst was then introduced to the flask through a subsurface dipleg prior to hydrogen peroxide addition. 84.0 (0.94 mol) Grams of 35% hydrogen peroxide (4% excess) was fed over a 40-minute period. The reaction was allowed to proceed adiabatically until the temperature of the reaction mass reached a maximum temperature of 68° C. At this point the reaction mass began to cool because the reaction was essentially completed. Within 3 hours of introduction of catalyst and hydrogen peroxide, the reaction was completed. The total nitrosamine content of the sample was 8 ppb.

EXAMPLE 4

In this procedure carbon dioxide catalyst was introduced slowly over time to a system containing amine, water, peroxide and chelating agent. The rate of reaction or rate of heat generation can be controlled simply by control of catalyst feed rate, which in turn can be controlled with reference to the pH of the system. Thus, combined in an insulated round bottom flask at ambient temperature were 452 g ADMA-10 amine (2.44 mol), 922 mL tap water, 1.13 g DTPA (2.9 mmol), and 244.5 g 35% hydrogen peroxide. The pH of the reaction mixture was maintained at 8 by portionwise addition of carbon dioxide to the reaction mixture. A total of 3.8 g carbon dioxide was added. Maximum temperature (77° C.) was achieved in 35 minutes.

It can be seen that among the improvements made possible by this invention are the following:
1) Faster reaction and shorter reaction period,
2) Lower nitrosoamine values despite in situ generation of higher temperatures,
3) Very low metal content such as sodium in the amine oxide product, and
4) Very low residual free amine in the amine oxide product.

In order to still further appreciate the improvements made possible by the practice of this invention, there are summarized in the table the results of analyses of approximately 30 wt % aqueous tertiary amine oxide products available from various commercial sources. These products were as follows:

BARLOX 12 amine oxide (Lonza Inc.) (Specification: 29.6 wt % lauryl dimethyl tertiary amine oxide);

BARLOX 14 amine oxide (Lonza Inc.) (Specification: 31.4 wt % myristyl dimethyl tertiary amine oxide);

AMMONYX LO amine oxide (Stephan Co.) (Specification: 30.6 wt % lauryl dimethyl tertiary amine oxide);

AMMONYX MO amine oxide (Specification: 30.1 wt % myristyl dimethyl tertiary amine oxide); and EMCOL LO amine oxide (Witco Corp.) (Specification: 30.1 wt % lauryl dimethyl tertiary amine oxide).

TABLE

| Amine Oxide | Na, ppm | Fe, ppm | Ni, ppm | Amine, wt % | $H_2O_2$, wt % |
| --- | --- | --- | --- | --- | --- |
| BARLOX 12 | 520 | 2.54 | <0.4 | 0.53 | 0.07 |
| BARLOX 14 | 407 | 2.59 | <0.4 | 0.56 | 0.09 |
| AMMONYX LO | 358 | <0.5 | <0.4 | 0.45 | 0.04 |
| AMMONYX MO | 120 | 2.67 | <0.4 | 0.22 | 0.0 |
| EMCOL LO | 564 | 0.11 | <0.3 | 1.82 | 0.09 |

In the specification and claims hereof, nitrosamine content of the tertiary amine oxide product compositions of this invention refers to the total nitrosamine content of the product, reported as —NNO species. Such species has a molecular weight of 44. Thus the nitrosamine content, if any, of the tertiary amine oxide product compositions of this invention is independent of the organic groups to which the —NNO species is attached.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus, the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises," "is," etc.), the reference is to the substance, component or ingredient as it existed at the time just before it was first contacted, blended or mixed with one or more other substances, components and/or ingredients in accordance with the present disclosure. The fact that the substance, component or ingredient may have lost its original identity through a chemical reaction or transformation during the course of such contacting, blending or mixing operations is thus wholly immaterial for an accurate understanding and appreciation of this disclosure and the claims thereof.

Likewise, the process of this invention produces "tertiary amine oxide" in an aqueous medium. By this is meant that if the water is removed one will recover tertiary amine oxide as a chemical product. While the "tertiary amine oxide" is in solution it may possibly be solvated, hydrated, complexed, or otherwise altered in chemical makeup, and if such actually happens, the claims hereinafter are intended to cover any such natural consequence of carrying out the process of this invention in the proper manner as described herein. Thus it matters not if any such salvation, hydration, or other alteration in chemical makeup of the "tertiary amine oxide" occurs while in the aqueous medium as long as the process is being carried out properly as described and claimed herein. In short, the product of the process is identified as chemists identify products, and not as lawyers or others might seek to identify them.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A process for producing tertiary amine oxide which comprises oxidizing tertiary amine with hydrogen peroxide in an aqueous reaction medium, the aqueous reaction medium having been formed or being formed from tertiary amine, aqueous hydrogen peroxide, carbon dioxide, and optionally chelating agent and/or additional water, the exothermic oxidation reaction being initiated at a temperature in the range of about 15 to about 25° C., and while agitating the reaction mixture, allowing the temperature of the reaction mixture to rise adiabatically to a temperature in the range of about 50 to about 100° C., such that tertiary amine oxide is produced.

2. A process according to claim 1 wherein the reaction is initiated at about room temperature and wherein the temperature to which the reaction mixture rises adiabatically is in the range of about 60 to about 80° C.

3. A process according to claim 1 wherein the aqueous reaction medium is formed by mixing together tertiary amine, carbon dioxide, and optionally chelating agent and/or water, and then introducing aqueous hydrogen peroxide into the reaction mixture to initiate the exothermic reaction.

4. A process according to claim 3 wherein the reaction is initiated at about room temperature and wherein the temperature to which the reaction mixture rises adiabatically is in the range of about 60 to about 80° C.

5. A process according to claim 3 wherein hydrogen peroxide is introduced portionwise continuously and/or intermittently into the reaction mixture.

6. A process according to claim 1 wherein chelating agent is included in said reaction medium.

7. A process according to claim 1 wherein the aqueous reaction medium is formed by mixing together tertiary amine, carbon dioxide, chelating agent, and optionally water, and then introducing aqueous hydrogen peroxide into the reaction mixture to initiate the exothermic reaction; wherein the reaction is initiated at about room temperature; and wherein the temperature to which the reaction mixture rises adiabatically is in the range of about 60 to about 80° C.

8. A process according to claim 7 wherein hydrogen peroxide is introduced portionwise, continuously and/or intermittently, into the reaction mixture.

9. A process according to claim 1 wherein the aqueous reaction medium is formed introducing tertiary amine, and optionally chelating agent and/or water, into a reactor, and then introducing concurrently or in any sequence, aqueous hydrogen peroxide and carbon dioxide to initiate the exothermic reaction.

10. A process according to claim 9 wherein hydrogen peroxide is introduced portionwise, continuously and/or intermittently, into the reaction mixture.

11. A process according to claim 9 wherein hydrogen peroxide and carbon dioxide are introduced portionwise, continuously and/or intermittently, into the reaction mixture.

12. A process according to claim 1 wherein the aqueous reaction medium is formed by mixing together tertiary amine, aqueous hydrogen peroxide, and optionally chelating agent and/or additional water, and then introducing carbon dioxide to initiate the exothermic reaction.

13. A process according to claim 1 wherein the tertiary amine has the formula $R^1R^2R^3N$ where $R^1$ is a methyl or ethyl group, $R^2$ contains in the range of about 8 to about 20 carbon atoms and is either an alkyl group or an unsaturated aliphatic hydrocarbyl group in which the unsaturation is from 1 to 3 olefinic double bonds, and $R^3$ is, independently, a methyl group, an ethyl group, an alkyl group containing in the range of about 8 to about 20 carbon atoms, or an unsaturated aliphatic hydrocarbyl group containing in the range of about 8 to about 20 carbon atoms and in which the unsaturation is from 1 to 3 olefinic double bonds.

14. A process according to claim 1 wherein the tertiary amine has the formula $R^1R^2R^3N$ where $R^1$ is a methyl group, $R^2$ is an alkyl group containing in the range of about 8 to about 20 carbon atoms, and $R^3$ is, independently, a methyl group or an alkyl group containing in the range of about 8 to about 20 carbon atoms.

15. A process according to claim 1 wherein the tertiary amine is a dimethyl long chain alkyl amine in which the long chain alkyl group contains in the range of 8 to 20 carbon atoms.

16. A process according to claim 1 wherein the hydrogen peroxide is a 30 to 70% aqueous hydrogen peroxide solution.

17. A process according to claim 1 wherein the chelating agent is diethylene triamine pentaacetic acid, ethylene diamine tetraacetic acid, or a water-soluble salt of either of them, or a combination of any two or more of the foregoing.

18. A process according to claim 1 wherein the amount of carbon dioxide used in forming said mixture is such that the pH of said reaction mixture is in the range of about 7 to about 8.

19. A process according to claim 1 wherein the reaction is performed in a thermally insulated reactor.

20. A process according to claim 1 wherein the nitrosamine content of the tertiary amine oxide produced is 30 parts per billion (wt/wt) or less.

21. A process according to claim 1 wherein:
a) the reaction is initiated at about room temperature;
b) the temperature to which the reaction mixture rises adiabatically is in the range of about 60 to about 80° C.;
c) the tertiary amine is a dimethyl long chain alkyl amine in which the long chain alkyl group contains in the range of about 8 to about 20 carbon atoms;
d) the hydrogen peroxide is a 30 to 70% aqueous hydrogen peroxide solution;
e) the amount of carbon dioxide used in forming said mixture is such that the pH of said reaction mixture is in the range of about 7 to about 8; and
f) the reaction is performed in a thermally insulated reactor.

22. A process according to claim 21 wherein a chelating agent is included in said reaction mixture, and wherein the chelating agent is diethylene triamine pentaacetic acid or a water-soluble salt thereof.

23. A process according to claim 21 wherein the nitrosamine content of the tertiary amine oxide produced is 30 parts per billion (wt/wt) or less.

24. A process for producing tertiary amine oxide which comprises mixing together tertiary amine, aqueous hydrogen peroxide, chelating agent, and carbon dioxide at a temperature in the range of about 15 to about 25° C., such that exothermic oxidation of tertiary amine to tertiary amine oxide is initiated, and while agitating the reaction mixture, allowing the temperature of the reaction mixture to rise adiabatically to a temperature in the range of about 50 to about 100° C.

25. A process according to claim 24 wherein the reaction is initiated at about room temperature and wherein the temperature to which the reaction mixture rises adiabatically is in the range of about 60 to about 80° C.

26. A process according to claim 24 wherein:
a) the reaction is initiated at about room temperature;
b) the temperature to which the reaction mixture rises adiabatically is in the range of about 60 to about 80° C.;
c) the tertiary amine is a dimethyl long chain alkyl amine in which the long chain alkyl group contains in the range of 8 to 20 carbon atoms;
d) the amount of carbon dioxide used in forming said mixture is such that the pH of said reaction mixture is in the range of about 7 to about 8; and
e) the reaction is performed in a thermally insulated reactor.

27. A process according to claim 26 wherein the chelating agent is diethylene triamine pentaacetic acid or a water-soluble salt thereof.

28. A process according to claim 27 wherein the nitrosamine content of the tertiary amine oxide produced is 30 parts per billion (wt/wt) or less.

29. A process for producing tertiary amine oxide which comprises introducing carbon dioxide into an aqueous mixture which initially is at a temperature in the range of about 15 to about 25° C., and which was formed from tertiary amine, aqueous hydrogen peroxide, chelating agent, and optionally additional water, until the pH of the mixture is in the range of about 7 to about 8, such that exothermic oxidation of tertiary amine to tertiary amine oxide is initiated, and while agitating the reaction mixture, allowing the temperature of the reaction mixture to rise adiabatically to a temperature in the range of about 70 to about 90° C.

30. A process according to claim 14 wherein the reaction is initiated at about ambient room temperature and wherein the temperature to which the reaction mixture rises adiabatically is in the range of about 70 to about 80° C.

31. A process for producing tertiary amine oxide which comprises introducing carbon dioxide into an aqueous mixture which initially is at a temperature in the range of about 15 to about 25° C., and which was formed from tertiary amine, chelating agent, and optionally additional water, until the pH of the mixture is in the range of about 7 to about 8, and then initiating continuous and/or intermittent portionwise feed of aqueous hydrogen peroxide such that exothermic oxidation of tertiary amine to tertiary amine oxide is initiated, and while agitating the reaction mixture, allowing the temperature of the reaction mixture to rise adiabatically to a temperature in the range of about 70 to about 90° C.

32. A process according to claim 31 wherein the reaction is initiated at about ambient room temperature and wherein the temperature to which the reaction mixture rises adiabatically is in the range of about 70 to about 80° C.

33. A process according to claim 31 wherein:
a) the reaction is initiated at about room temperature;
b) the temperature to which the reaction mixture rises adiabatically is in the range of about 60 to about 80° C.;

c) the tertiary amine is a dimethyl long chain alkyl amine in which the long chain alkyl group contains in the range of about 8 to about 20 carbon atoms;

d) the hydrogen peroxide is a 30 to 70% aqueous hydrogen peroxide solution; and e) the reaction is performed in a thermally insulated reactor.

34. A process according to claim 33 wherein the chelating agent is diethylene triamine pentaacetic acid or a water-soluble salt thereof.

35. A process according to claim 34 wherein the nitrosamine content of the tertiary amine oxide produced is 30 parts per billion (wt/wt) or less.

36. A process for producing tertiary amine oxide which comprises oxidizing tertiary amine with hydrogen peroxide in an aqueous reaction medium, the aqueous reaction medium having been formed or being formed from tertiary amine, aqueous hydrogen peroxide, carbon dioxide, and optionally chelating agent and/or additional water, the exothermic oxidation reaction being initiated at a temperature in the range of about 1 to about 25° C., and while agitating the reaction mixture, applying a controlled limited amount of heat energy to the reaction mixture and maintaining a substantially uniform temperature throughout the agitated reaction mixture whereby at any given moment in time the temperature differential within the reaction mixture is no greater than about 5° C., such that the temperature of the reaction mixture is increased to a maximum temperature in the range of about 50 to about 100° C., and such that tertiary amine oxide is produced, the major amount of the heat energy causing the increase in temperature of the reaction mixture being derived from the exothermic reaction itself, with the balance of the thermal energy causing such temperature increase being supplied by the application of said controlled limited amount of thermal energy to the reaction mixture.

37. A process according to claim 36 wherein said temperature differential is no greater than 2° C., and wherein the nitrosamine content of the tertiary amine oxide produced is 30 parts per billion (wt/wt) or less.

* * * * *